(12) United States Patent
Gering

(10) Patent No.: US 8,125,484 B2
(45) Date of Patent: Feb. 28, 2012

(54) METHOD, APPARATUS AND USER INTERFACE FOR DETERMINING AN ARTERIAL INPUT FUNCTION USED FOR CALCULATING HEMODYNAMIC PARAMETERS

(75) Inventor: David T. Gering, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1131 days.

(21) Appl. No.: 11/558,767

(22) Filed: Nov. 10, 2006

(65) Prior Publication Data

US 2008/0114234 A1 May 15, 2008

(51) Int. Cl.
*G06T 11/20* (2006.01)
(52) U.S. Cl. ........................................ 345/440; 600/411
(58) Field of Classification Search .................. 600/411; 345/440
See application file for complete search history.

(56) References Cited

U.S. PATENT DOCUMENTS

| | | | |
|---|---|---|---|
| 7,069,068 B1 * | 6/2006 | Ostergaard | 600/420 |
| 7,595,801 B1 * | 9/2009 | Cherkas | 345/440 |
| 2006/0033752 A1 | 2/2006 | Gering et al. | |

OTHER PUBLICATIONS

Syngo MR 2006T Operator Manual, 2005.*
Lorenz, Cory. Automated Perfusion-weighted MRI Metrics via Localized Arterial Input Functions. Thesis. Massachusetts Institute of Technology, Dept. of Electrical Engineering and Computer Science, 2004.*
T.J. Carroll, H.A. Rowley, V.M. Haughton, "Automatic Calculation of the Arterial Input Function for Cerebral Perfusion Imaging With MR Imaging," Radiology May 2003; 227:593-600.
Ostergaard, Leif, et al., High Resolution Measurement of Cerebral Blood Flow using Intravascular Tracer Bolus Passages. Part I: Mathematical Approach and Statistical Analysis. MRM 36: 715-725 (1996).

* cited by examiner

*Primary Examiner* — Xiao M. Wu
*Assistant Examiner* — Scott E Sonners
(74) *Attorney, Agent, or Firm* — The Small Patent Law Group; Dean D. Small

(57) ABSTRACT

A graphical user interface and method allows a user to interactively select an arterial input function. An anatomical image and time-course data corresponding to a selected region of interest are displayed simultaneously. The time-course data is displayed as an array of graphs, annotated with best-fit curves and parameters derived from fitting the time-course data. The region displayed in the graphs may be updated by panning and zooming with a mouse in the image. Time-course data corresponding to a graph is selected for use in deriving an arterial input function. The arterial input function is used to calculate maps of hemodynamic parameters.

23 Claims, 7 Drawing Sheets

METHOD, APPARATUS AND USER INTERFACE FOR DETERMINING AN ARTERIAL INPUT FUNCTION USED FOR CALCULATING HEMODYNAMIC PARAMETERS

TECHNICAL FIELD

The present invention relates generally to magnetic resonance imaging (MRI) systems and in particular, to a graphical user interface, apparatus and method for determining an arterial input function which may be used to calculate hemodynamic parameters such as regional blood flow and regional blood volume.

BACKGROUND

Dynamic contrast enhanced MRI is performed to characterize tissue perfusion by observing and analyzing the passage of a bolus of contrast agent through the tissue. MR images are acquired at regular intervals during a time period that begins prior to the injection of the contrast agent, and extends through the contrast agent's passage through the tissue under study. To acquire the images, a pulse sequence is selected that produces images whose signal intensity is proportional to the concentration of contrast agent in the tissue, such as a perfusion-weighted echo-planar imaging (EPI) sequence. The MRI signal intensity of the tissue during this time period may be plotted versus time, to produce a time-course for the tissue. Time-courses may be constructed for single pixels, or for groups of neighboring pixels by combining the signal from multiple pixels. The signal intensity may be converted to a concentration of contrast agent with some simplifying assumptions regarding the tissue relaxivity.

For analytical purposes, the tissue vasculature may be modeled as a linear, time-invariant system (LTI). The output of a LTI system may be computed as the convolution of an input function with a transfer function. In this case, the input function is the contrast agent concentration in an artery feeding the tissue under study, referred to as the Arterial Input Function (AIF). The AIF is typically determined by selecting pixels corresponding to a feeding artery (or arteriole), extracting the time-course for the corresponding voxels, and converting the signal intensity to a concentration of contrast agent. An output function is computed in a similar manner from the time-course for the tissue voxels. A transfer function may be computed from an AIF and an output function. The transfer function describes the transformation of the input to the output, and reflects aspects of the tissue vasculature, such as regional blood flow, regional blood vessel density, and average regional vessel permeability, for example.

The transfer function is recovered by performing a deconvolution using the AIF and output concentration curves. Typically, a transfer function is calculated for every tissue voxel contributing to an image, on a voxel-by-voxel basis. From the transfer functions, maps of hemodynamic parameters may be computed and may be overlaid on an anatomical image for review. The maps of the hemodynamic parameters are known as parametric maps. A typical perfusion study in the brain may include maps of regional cerebral blood flow (rCBF), mean transit time (MTT), and regional Cerebral Blood Volume (rCBV), for example.

To obtain meaningful results for the parametric maps, it is important to choose an appropriate AIF, i.e., an AIF that corresponds to a feeding vessel for a tissue. For brain tumor perfusion studies, the AIF is typically chosen to correspond to a primary artery feeding the tumor. In the setting of a stroke study, the computation of parametric maps may require using different AIFs corresponding to the appropriate regional feeding vessels for different regions of the brain. Typically, a skilled reviewer, for example, a radiologist, examines an image to locate pixels corresponding to a blood vessel, and examines the time-course for those pixels. If the time-course exhibits the expected characteristics for a feeding vessel, it may be chosen as an AIF for the calculation of hemodynamic parameters in the surrounding tissue. The process of selecting AIFs may be time consuming and may require several iterations before the appropriate AIFs are identified. Methods for an automatic selection of an AIF are known in the prior art, however, these methods typically rely only on the mathematical characteristics of a time-course as a basis for selecting an appropriate AIF. Such automatic methods do not benefit from a reviewer's knowledge about the pertinent anatomy and physiology of the tissue under study. Accordingly, it would be advantageous to provide a user interface or tool that allows a reviewer or user, such as a radiologist, to interactively select an AIF and view parametric maps based on the selected AIF in real time.

BRIEF DESCRIPTION OF THE INVENTION

In accordance with an embodiment, a method for determining an arterial input function from a magnetic resonance image dataset includes providing a user interface configured to display at least one magnetic resonance image from the magnetic resonance image dataset and a plurality of time-course graphs simultaneously, the plurality of time-course graphs associated with a selected region of the at least one magnetic resonance image and each time-course graph having associated time-course data, annotating at least one time-course graph with at least one element that indicates fitness of the time-course data associated with the at least one time-course graph for use in deriving an arterial input function, receiving a selection of a time-course graph from the plurality of time-course graphs, and deriving an arterial input function from the time-course data associated with the selected time-course graph.

In accordance with another embodiment, a computer-readable medium having computer-executable instructions for determining an arterial input function from a magnetic resonance image dataset includes program code for providing a user interface configured to display at least one magnetic resonance image from the magnetic resonance image dataset and a plurality of time-course graphs simultaneously, the plurality of time-course graphs associated with a selected region of the at least one magnetic resonance image and each time-course graph having associated time-course data, program code for annotating at least one time-course graph with at least one element that indicates fitness of the time-course data associated with the at least one time-course graph for use in deriving an arterial input function, program code for receiving a selection of a time-course graph from the plurality of time-course graphs, and program code for deriving an arterial input function from the time-course data associated with the selected time-course graph.

In accordance with another embodiment, an apparatus for determining an arterial input function from a magnetic resonance image dataset includes a user interface configured to display at least one magnetic resonance image from the magnetic resonance image dataset and a plurality of annotated time-course graphs simultaneously and to receive a selection of a time-course graph from the plurality of time-course graphs to be used in deriving an arterial input function, wherein the plurality of annotated time-course graphs is associated with a selected region of the at least one magnetic resonance image.

In accordance with another embodiment, an apparatus for determining an arterial input function from a magnetic resonance image dataset includes a processing unit programmed to execute a user interface configured to display at least one magnetic resonance image from the dataset and a plurality of annotated time-course graphs simultaneously and to receive a selection of a time-course graph from the plurality of time-course graphs to be used in deriving an arterial input function, wherein the plurality of annotated time-course graphs is associated with a selected region of the at least one magnetic resonance image.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

A graphical user interface (GUI) for simultaneously displaying anatomical magnetic resonance (MR) images, time-course data for selected regions of an MR image, and parametric images is configured to allow a user (e.g., a radiologist) to interactively select an arterial input function (AIF). The user interface provides the user with the ability to view simultaneously (e.g., side-by-side) anatomical MR images, and time-course data corresponding to a selected pixel or group of pixels from the images. The time-course data or portions thereof are automatically fitted to polynomials and the displayed time-course data may be annotated with best-fit curves. Mathematical parameters derived from the curve-fitting and other parameters related to properties of the time-course may also be displayed to assist the user in determining whether a time-course may be a suitable choice for an AIF. Parametric maps calculated using a selected AIF may also be displayed. A navigation tool, including image navigation features such as panning and zooming, is included so that the user may update the selection of pixels for the time-course data. For example, the navigation tool may be configured so that a user may navigate the image and time-course data using only mouse controls. Such an interactive GUI enables a user to supplement the automatically calculated curve-fitting parameters with his/her knowledge of the local anatomy and physiology (e.g., a knowledge of which blood vessels typically feed a particular region of the brain) in order to select an appropriate AIF for a region.

Figure 1:
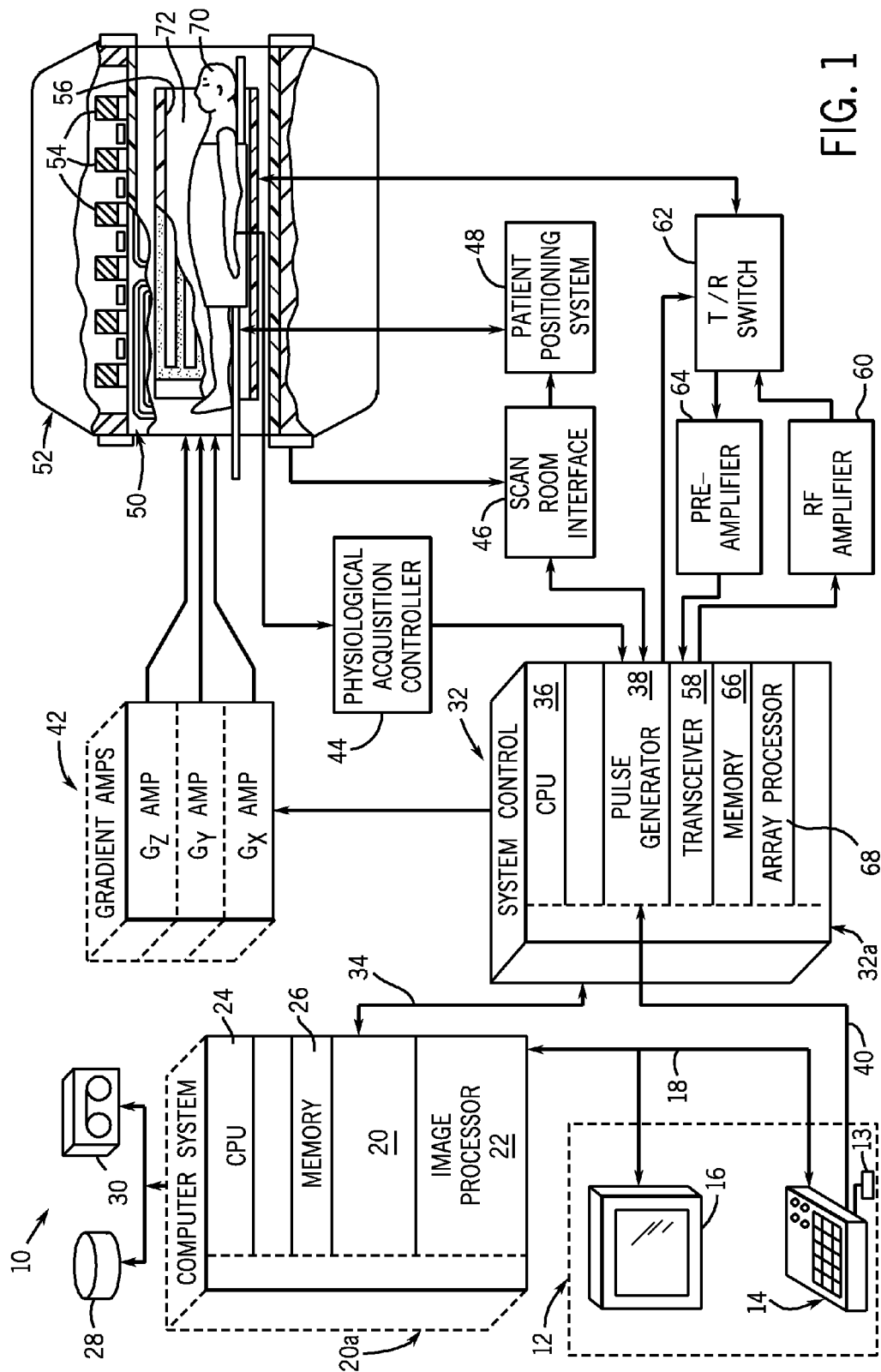
FIG. 1 is a schematic block diagram of an exemplary magnetic resonance imaging system.

FIG. 1 is a schematic block diagram of an exemplary magnetic resonance imaging system. The operation of MRI system 10 is controlled from an operator console 12 that includes a keyboard or other input device 13, a control panel 14, and a display 16. The console 12 communicates through a link 18 with a computer system 20 and provides an interface for an operator to prescribe MRI scans, display the resultant images, perform image processing on the images, and archive data and images. The computer system 20 includes a number of modules that communicate with each other through electrical and/or data connections, for example such as are provided by using a backplane 20a. Data connections may be direct wired links, or may be fiberoptic connections or wireless communication links or the like. These modules include an image processor module 22, a CPU module 24 and a memory module 26. Memory module 26 may be, for example, a frame buffer for storing image data arrays as known in the art. In an alternative embodiment, the image processor module 22 may be replaced by image processing functionality on the CPU module 24. The computer system 20 is linked to archival media devices, such as disk storage 28 and tape drive 30 for storage of image data and programs, and communicates with a separate system control computer 32 through a high speed serial link 34. Archival media include but are not limited to random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which may be used to store the desired instructions and which can be accessed by computer system 20, including by internet or other computer network forms of access. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links, or may be fiberoptic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. It is through link 40 that the system control computer 32 receives commands from the operator to indicate the scan sequence that is to be performed. The pulse generator module 38 operates the system components that play out (i.e., perform) the desired pulse sequence and produces data called RF waveforms which control the timing, strength and shape of the RF pulses to be used, and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and a whole-body RF coil 56. A patient or imaging subject 70 may be positioned within a cylindrical imaging volume 72 of the magnet assembly 52. A transceiver module 58 in the system control computer 32 produces pulses that are amplified by an RF amplifier 60 and coupled to the RF coils 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the coil during the receive mode. The transmit/receive switch 62 can also enable a separate RF coil (for example, a surface coil) to be used in either the transmit or receive mode.

The MR signals sensed by the RF coil 56 are digitized by the transceiver module 58 and transferred to a memory module 66 in the system control computer 32. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the high speed link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on display 16.

Various pulse sequences that are sensitive to perfusion may be used to perform a dynamic contrast enhanced MRI of a tissue, for example the brain, breast, or musculoskeletal tissues. The pulse sequences may be used with the above-described MR system, or any similar or equivalent system for obtaining MR images, to perform a perfusion study. For example, an echo planar imaging (EPI) pulse sequence may be used to acquire a series of perfusion-weighted images of the brain. Alternatively, other perfusion-weighted sequences may be used. For example, it may be of interest to perform a perfusion study of the finger joints in the setting of rheumatoid arthritis. For this application, a perfusion-weighted, GRE-based sequence, may be used.

Figure 2:
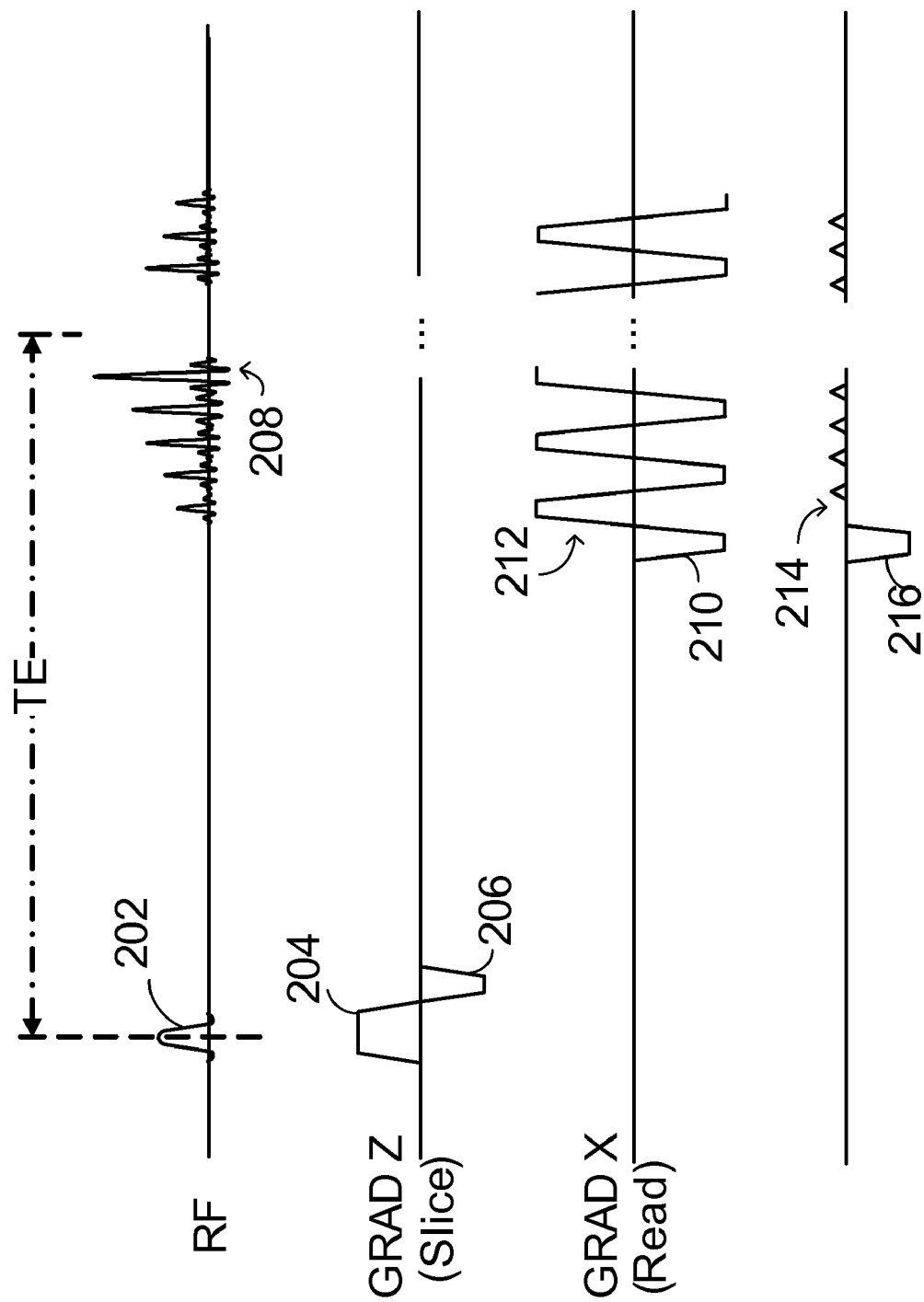
FIG. 2 is a pulse sequence diagram for an exemplary echo planar imaging (EPI) pulse sequence in accordance with an embodiment.

FIG. 2 is a pulse sequence diagram for an exemplary echo planar imaging (EPI) pulse sequence in accordance with an embodiment. The EPI pulse sequence may be used to acquire a series of perfusion-weighted images of, for example, the brain. A RF excitation pulse 202 is applied in the presence of a Gz slice select gradient pulse 204 to produce transverse magnetization in a slice through the brain. The excited spins are rephased by a negative lobe 206 on the slice select gradient Gz and then a time interval determined by a scanner operator's choice of TE elapses before the readout begins. Multiple separate MR signals, indicated generally at 208, are acquired during the EPI pulse sequence. Typically, 64 to 128 MR signals are acquired for a single image. Each MR echo signal 208 is separately phase-encoded to scan ky-space from $ky=-ky_{max}$ to $ky=+ky_{max}$ in monotonic order. The readout is positioned such that the view acquired at $ky=0$ occurs at the desired echo time (TE).

The MR echo signals 208 are gradient-recalled echoes produced by the application of an oscillating Gx readout gradient field 212. The readout sequence is started with a negative readout gradient lobe 210 and the echo signals 208 are produced as the readout gradient oscillates between positive and negative values. Each MR echo signal 208 is sampled rapidly during each readout gradient pulse 212. The successive MR echo signals 208 are separately phase-encoded by a series of Gy phase encoding gradient pulses 214. The first pulse is a negative lobe 216 that occurs before the echo signals are acquired to encode the first view at $ky=-ky_{max}$. Subsequent phase encoding pulses 214 occur as the readout gradient pulses 212 switch polarity, and they step the phase encoding monotonically upward through ky space. The k-space data is Fourier transformed along both of its dimensions (ky and kx) to produce an image of the MR signal magnitude. This pulse sequence is repeated with varying slice positions, typically until slices covering the subject's brain are acquired. For most subjects, complete coverage of the brain may be achieved in 1 to 2 seconds using an EPI pulse sequence. This process is repeated during the period in which a contrast agent bolus makes a first pass through the brain tissue, resulting in a multiple slice, multiple time-point image dataset. As mentioned above, other fast pulse sequences that are sensitive to perfusion may alternatively be used.

Figure 3:
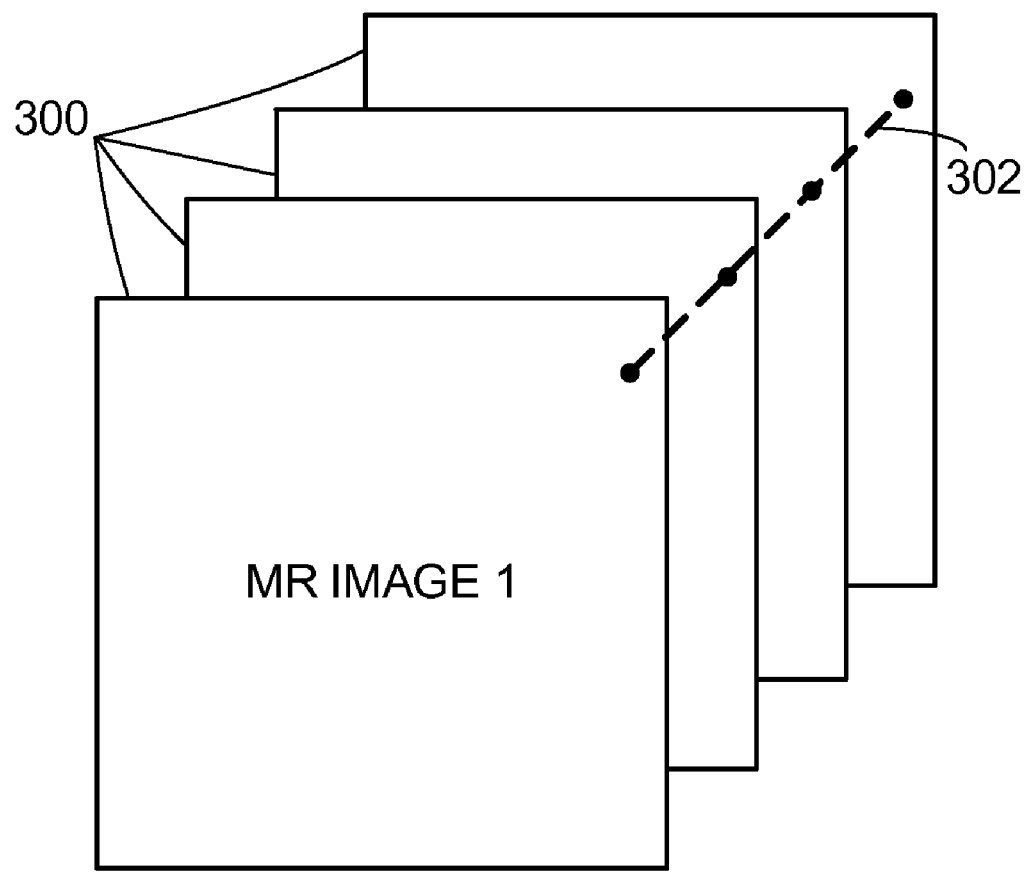
FIG. 3 is a schematic diagram of a dataset of images of a single slice acquired at multiple time points in a perfusion study in accordance with an embodiment.

FIG. 3 is a schematic diagram of a dataset of images of a single slice acquired at multiple time points in a perfusion study in accordance with an embodiment. For example, the dataset 300 may be a set of images of a single slice through the brain acquired in a perfusion study using multiple repetitions of a fast pulse sequence such as an EPI pulse sequence as described above with respect to FIG. 2. Each image corresponds to a time-point during the passage of the contrast bolus. By extracting the signal intensity for a particular image pixel from each image in the dataset 300, the signal intensity time-course, S(t), may be plotted for the tissue voxel corresponding to that pixel. This is indicated by the dashed line 302 in FIG. 3. The time-course may be used to derive an output function in a LTI model or equation for that voxel. Alternatively, the time-course may be used to derive an AIF for voxels thought to correspond to an appropriate feeding vessel. Parametric maps may be calculated based on an AIF (among other factors).

Figure 4:
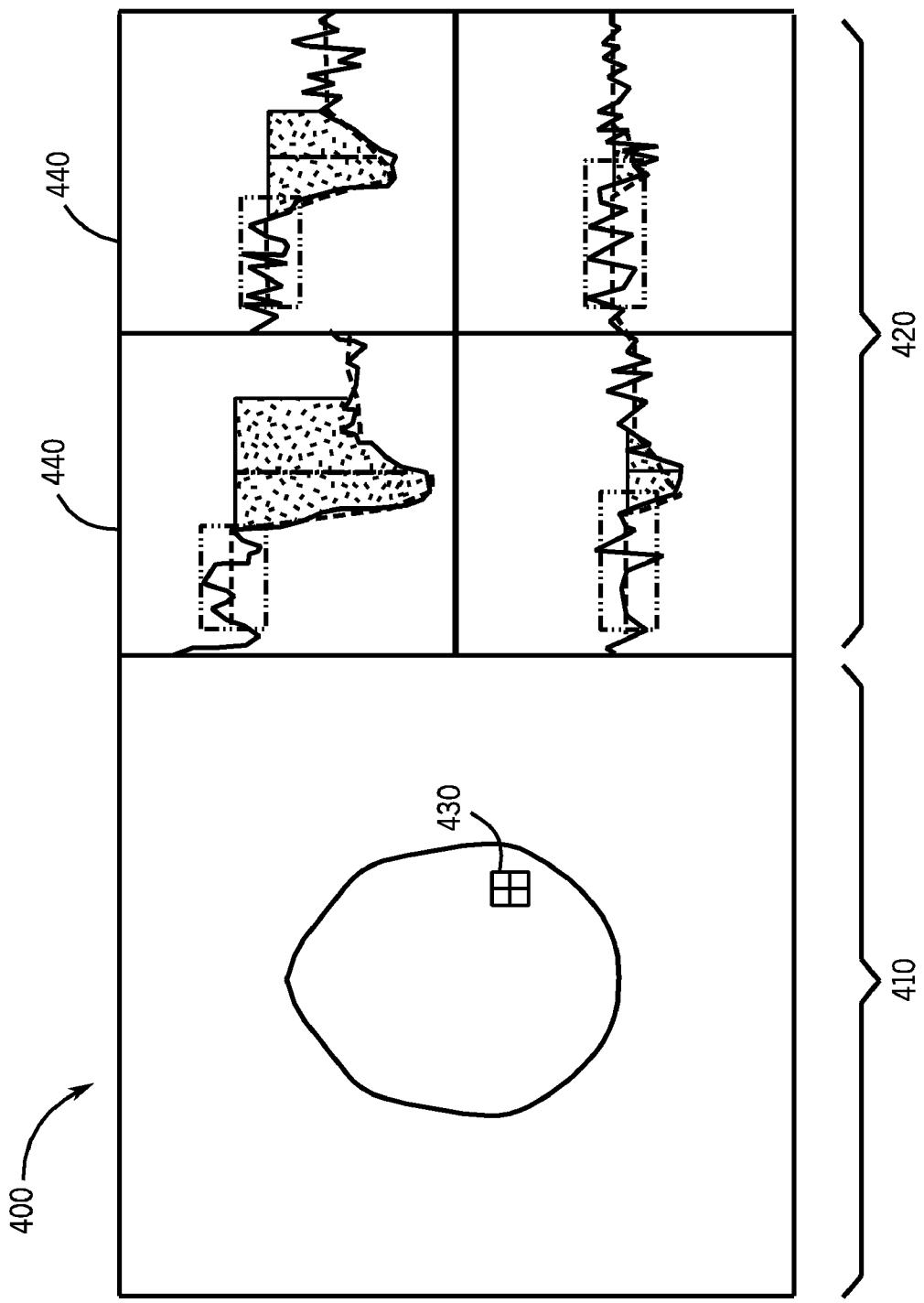
FIG. 4 shows an exemplary graphical user interface (GUI) displaying a magnetic resonance (MR) image side-by-side with an array of annotated time-course graphs in accordance with an embodiment.

A graphical user interface or tool may be configured to facilitate the selection or determination of an AIF. FIG. 4 shows an exemplary graphical user interface (GUI) displaying a MR image side-by-side with an array of annotated time-course graphs in accordance with an embodiment. In FIG. 4, the GUI 400 displays an anatomical MR image 410 of a head. Image 410 is an image from a selected dataset of images. Initially, the image 410 displayed in GUI 400 may be a default image such as the first image from the dataset. Alternatively, an image from the dataset corresponding to the peak contrast agent concentration may be displayed by default. An array of time-course graphs 420 is also displayed in GUI 400. A default region of interest from the image may be used to generate the array of time-course graphs 420 initially, for example, the region of interest may be the whole image 410 or a portion of the image 410. A portion of the image 410 to display as a default region of interest may be determined, for example, by automatically calculating time-courses for each pixel in the image, automatically selecting a pixel that meets pre-defined criteria for use as an AIF, and centering a region of interest with default sizing around the selected pixel. A default total number of time-course graphs may also be displayed initially. A user may select a different image from the image dataset to display using an input device, for example, by clicking a mouse-button to increment the image number from the image dataset. A different region of interest may be selected from image 410 using a navigation tool. The selected region may be highlighted using a visual indicator such as a box 430, other outlines, a pointer, etc. The visual indicator may also be highlighted using a color. The navigation tool may include a zoom feature that allows the user to "zoom" into the MR image 410 and display a portion of the MR image 410 at a higher resolution. The navigation tool may also include a panning feature to allow the user to change the portion of the image that is displayed by navigating around in the image. In one embodiment, the image navigation and selection functions may be accomplished using, for example, only mouse buttons. Once a region of the image 410 is selected, the selected region is used to generate the plurality of annotated time-course graphs 420. A user may select the number of time-course graphs generated and displayed in the array of time-course graphs 420.

Each time-course graph 440 shows time-course data for a pixel or combined time-course data from a group of neighboring pixels in the selected region of the image 410. The resolution of a time-course graph, (i.e., the number of pixels that are combined to calculate the time-course shown in the graph), is determined by the ratio of the number of pixels in the selected region to the total number of graphs displayed. At the highest resolution, each graph 440 corresponds to a single pixel. For lower resolutions, the time-courses from multiple neighboring pixels may be combined for display in each graph 440. Data from multiple graphs may be combined to construct a single time-course graph. Combining multiple curves into one can be accomplished by averaging the data from each individual pixel at each time-point, or by applying the scaling theorem. The scaling theorem prevents spurious artifacts by first spatially smoothing the data at each time-point using a Gaussian kernel, and then down-sampling to reduce the spatial extent of the data. Each time-course graph 440 is automatically generated based on the selected region of interest of image 410. When a new region of the image 410 is selected, time-course graphs for that region of interest are automatically calculated, updated and displayed in GUI 400.

Each time-course graph 440 in the array of time-course graphs 420 may be annotated with various elements that indicate or measure the fitness of the time-course data for use in deriving or defining an AIF. For example, a peak intensity measurement may be displayed, or a parameter related to the transit time for the contrast agent in the tissue may be derived from the curve and displayed. The elements or quantities used to annotate the time course graph 440 may also include, but are not limited to, signal baseline, arrival time, percentage of signal recovery or recovery relative to the baseline and negative enhancement integral. In addition, the time-course data from a graph may be automatically fitted to best-fit polynomial curves. The time-course data may be portioned into multiple segments and fitted separately to curves. Curve fitting methods generally known in the art may be used. In addition, a graph may be annotated with mathematical parameters derived from the curve-fitting. The mathematical parameters may be derived using methods generally known in the art. The amount and type of graph annotation may be changed by the user. For example, a user may elect to annotate a time-course graph 440 with a limited number of elements such as curves or parameters, to, for example, reduce clutter. In one embodiment, a fully annotated graph may be viewed by selecting (e.g., by clicking with an input device such as a mouse) an icon associated with the graph of interest.

Figure 5:
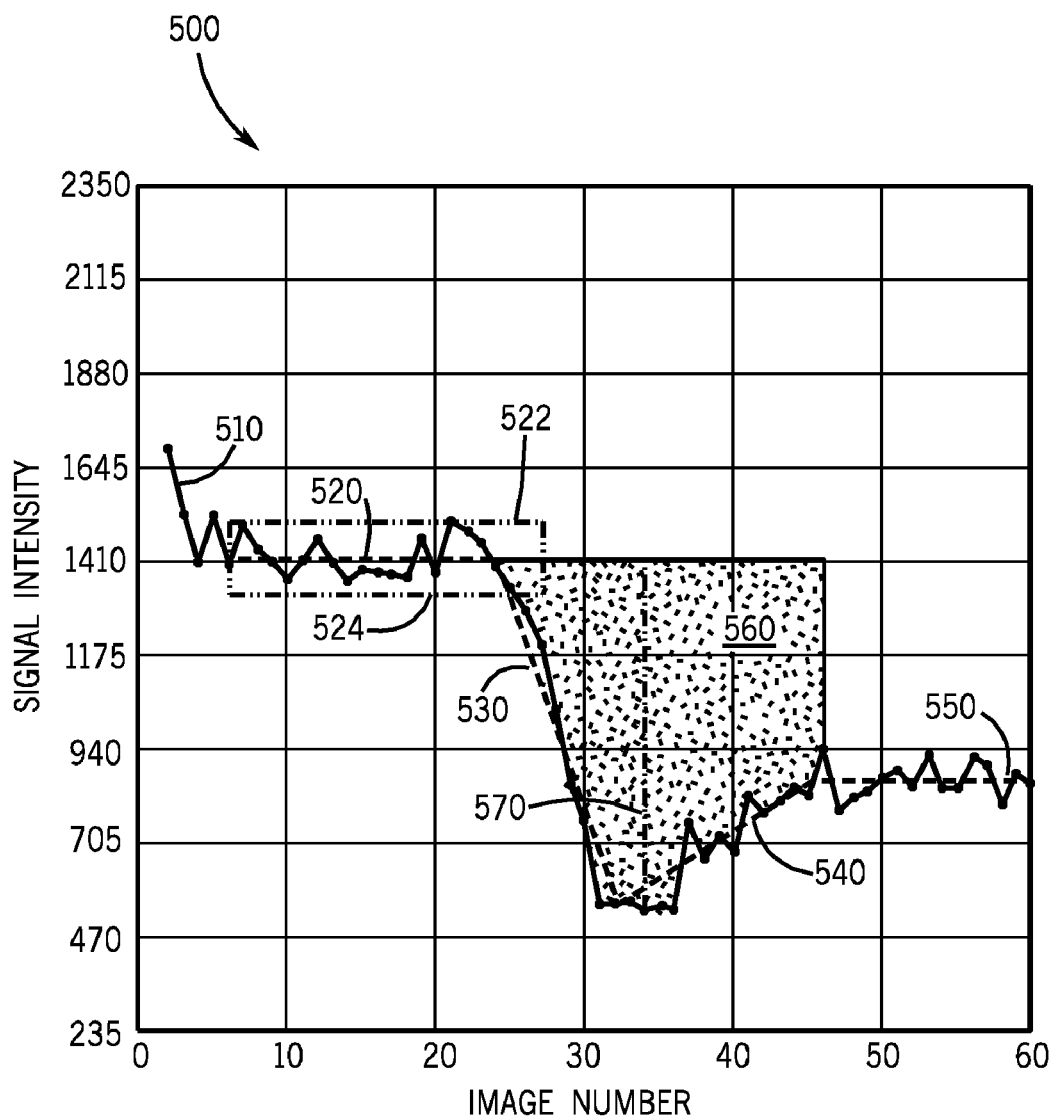
FIG. 5 shows an exemplary annotated graph of a signal intensity time-course from tissue in accordance with an embodiment.

FIG. 5 shows an exemplary annotated graph of a signal intensity time-course from tissue in accordance with an embodiment. Annotating the time-course graphs displayed in GUI 400 (shown in FIG. 4) with best-fit curves and/or mathematical parameters derived from the curve-fitting and/or other parameters characterizing the time-course aids the user in (or facilitates) identifying an appropriate AIF for a region of an image. In FIG. 5, signal intensity is plotted on the vertical axis, with each data point corresponding to a separate image, as labeled on the horizontal axis of the graph. The user may alternatively elect to display the computed concentration curves, $C(t)=-1/(k*TE)*\ln(S(t)/S(baseline))$, where $S(t)$ is the signal intensity versus time and k is a factor relating the MRI signal intensity to the concentration of contrast agent. The time-course 510 has been fitted to straight lines 520, 530, 540, and 550, in four independent segments. The first, horizontal straight line 520 corresponds to images 6 to 24 which occur prior to the injection of contrast agent. The level of the line 520 yields the mean signal intensity for those images, and the line 520 is defined as the signal baseline. A standard deviation of the signal intensities for these baseline images is also calculated, and is used to determine an upper threshold 522 and a lower threshold 524 for the baseline 520. At image 26, the signal intensity of the time-course drops below the lower threshold 524, marking the arrival time for the contrast bolus in the corresponding voxel. Quantities, such as the negative enhancement integral which is related to rCBV, may be computed from the curve fitting. The negative enhancement integral is shown in FIG. 5 as a shaded area 560. The peak height is shown in FIG. 5 as the vertical line 570 at image 34, and corresponds to the size of the decrease in signal intensity relative to the baseline. The recovery relative to baseline is shown in FIG. 5 as the horizontal best-fit line 550 for the data from images 45 to 60. As mentioned, each time-course graph and the annotation for each time-course graph displayed in GUI 400 (shown in FIG. 4) may be automatically generated based on the selected region of interest in the image 410 (shown in FIG. 4).

Returning to FIG. 4, a user may select an AIF by selecting (or indicating acceptance of) an appropriate time-course graph from the array of time-course graphs 420. For example, a time-course graph may be selected by clicking with a right mouse-button on the particular time-course graph. Selection of a particular time-course graph may be indicated in GUI 400 by using a visual indicator such as a heavier line-weight to outline the graph, or by using a unique background color, to update the display. Upon selection of a time-course graph for an AIF, parametric maps, for example, maps of rCBF, rCBV, MTT, etc., or any other parameter derived from the time-course or the fitted curves, (for example, the parameters indicated in FIG. 5), may be computed. These parametric maps may be displayed, for example, side-by-side with the time-course graphs, in place of the MR image. Alternatively, a parametric map may be displayed as a semi-transparent overlay on an anatomical MR image.

Figure 6:
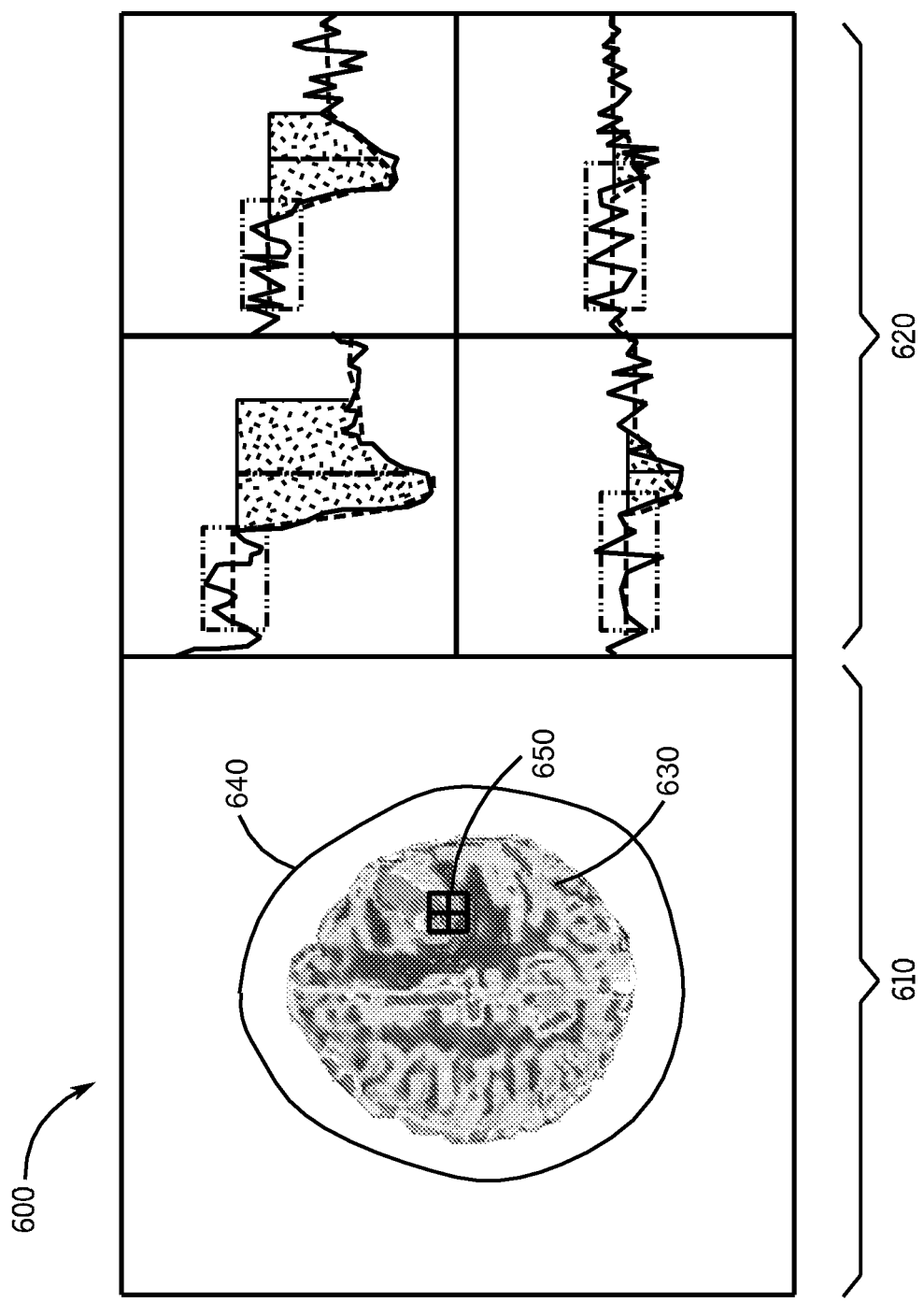
FIG. 6 shows the GUI of FIG. 4 displaying an exemplary parametric map overlaying an original MR image in accordance with an embodiment.

FIG. 6 shows the GUI of FIG. 4 displaying an exemplary parametric map overlaying an original MR image in accordance with an embodiment. A parametric map 630 is displayed in GUI 600 as a gray-scale overlay on the original MR image of a head 640 in image window 610. The GUI 600 also includes an array of time-course graphs 620 corresponding to the selected region of interest 650. Alternatively, parametric maps may be displayed as semi-transparent color overlays on the corresponding gray-scale anatomical images. Each time-course graph in the array of time-course graphs 620 may be provided with an indicator of a parametric value for the voxels associated with that graph, for example, a background color may be used to indicate the value of MTT for the corresponding voxels (not shown). The user may choose which hemodynamic parameter to display as a map in the image window 610 or as an indicator in the time-course graphs. Multiple parametric maps may be displayed simultaneously in the image window 610, or in separate image windows. If the user is not satisfied with the appearance of the parametric maps generated using the selected AIF, he/she may then choose a different time-course to generate an alternate AIF and the parametric maps may be recalculated.

For some anatomies, an AIF may only be properly associated as a feeding vessel with a region of tissue smaller than an image. In this case, parametric maps may be computed only within a region defined by the user as being associated with the selected AIF. Alternatively, a region of tissue that spans several adjacent images may be associated with a single feeding vessel. In this case, the region to be associated with an AIF may be outlined by a user on multiple adjacent images.

Referring now to FIG. 1 and FIG. 4, a computer program that creates and controls the GUI 400 may be executed by the CPU 24. The GUI 400 may be displayed on the MRI scanner display 16, and the image data may be accessed from memory 26. The input device 13 may be used to input information to the GUI 400, and may be used to perform the functions of the navigation tool. Computer-executable instructions for the GUI 400 and/or the MRI images may either be stored on the computer 20 itself, or may be stored on any form of digital information storage device, such as: electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the image data and which may be accessed by the MRI system 10, including by internet or other computer network forms of access.

In an alternative embodiment, the GUI 400 program may be executed by any computer (not shown) that is not a component of an MRI scanner, as long as the computer is able to access a MR perfusion dataset and has adequate computing capability. A mouse or other input device may be used to perform the functions of the navigation tool. The GUI may be displayed on any monitor (not shown) that can communicate with the computer. In another alternative embodiment, an external computing device may be used as a server communicating with an MRI scanner. The server may execute the GUI 400 program, using the scanner's display and input device.

Figure 7:
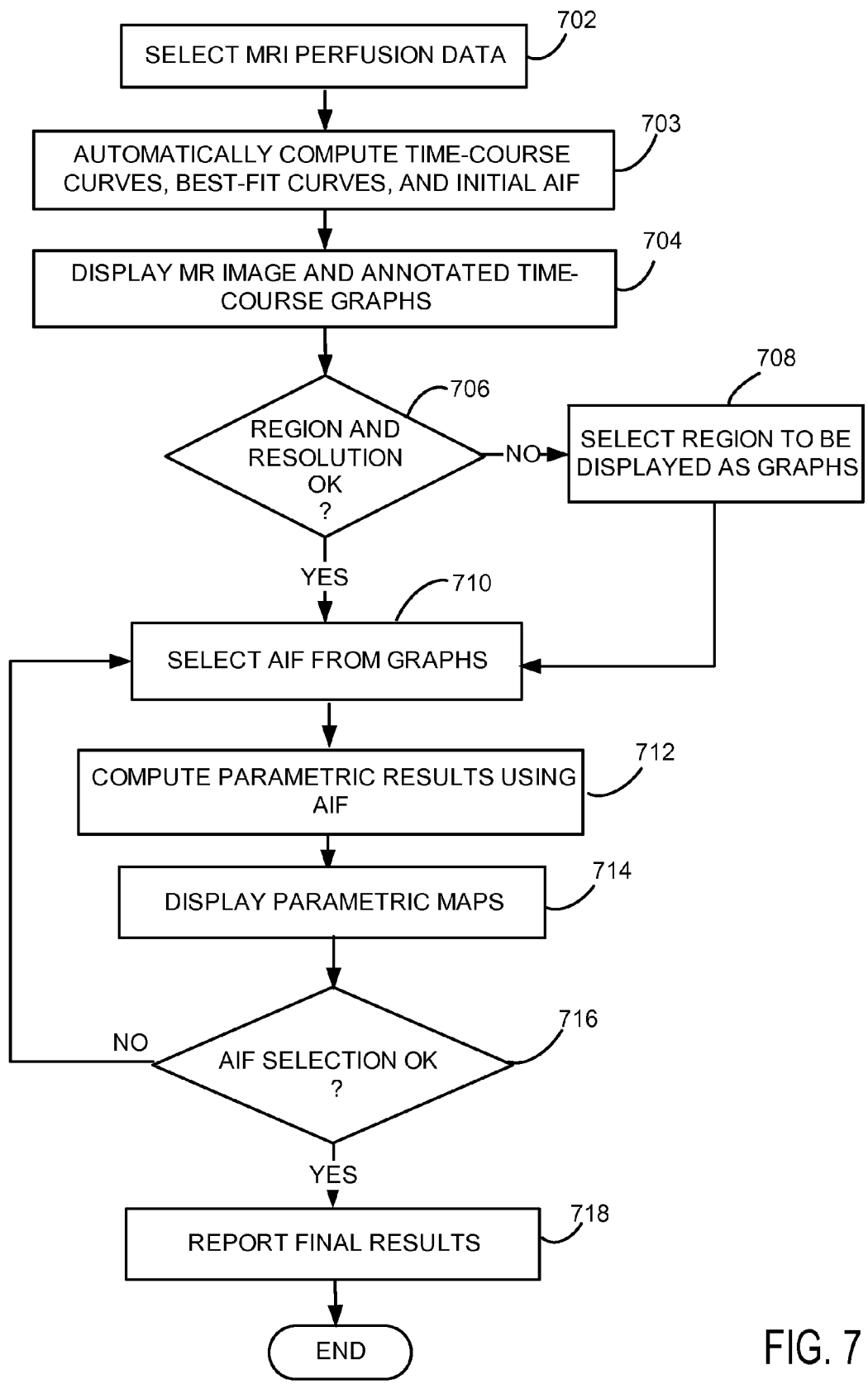
FIG. 7 is a flowchart showing an exemplary method for selecting an AIF and calculating hemodynamic parameters in accordance with an embodiment.

FIG. 7 is a flowchart showing an exemplary method for selecting an AIF and calculating hemodynamic parameters in accordance with an embodiment. At block 702, a user selects a dataset of MR images from a perfusion study for analysis. For example, a user may select a dataset using an input device and/or a user interface (e.g., provided on a display). At block 703, time-course graphs corresponding to the selected dataset are automatically generated based on a corresponding region of an image from the dataset along with elements or quantities used to annotate the time-course graphs. For example, a default total number of time-course graphs may be generated based on a default region of the image. The time-course data may be fitted using best-fit polynomial curves. The elements used to annotate the time-course graphs may include the best-fit polynomial curves and mathematical parameters that describe or indicate the fitness of the time-course for use as an AIF. The mathematical parameters may be derived from the fitting of the best-fit polynomial curves or by using other known algorithms. At block 704, a GUI is provided, e.g., on a display, that simultaneously displays an image from the dataset and the time-course graphs. The time-course graphs are annotated with the calculated best-fit curves and mathematical parameters describing the fitness of the time-course for use as an AIF. At blocks 706 and 708, the user interactively determines a region of pixels to display as time-course graphs and the resolution of the time-course graphs. At block 706, the user determines if the region of the image used to generate the time-course graphs and the resolution of the time-course graphs are the desired region and resolution. If the user determines a different region and resolution is desired, the user may select a region of the displayed image (i.e., a region of pixels) at block 708. The graphical user interface is also configured to allow the user to adjust the resolution of the time course graphs by changing the total number of time-course graphs in the display. Once the region and resolution are selected at block 708, the method proceeds to block 710. If, at block 706, the user determines that the region used to generate the time-course graphs and the resolution of the time-course graphs are the desired region and resolution, the method proceeds to block 710. At block 710, the user selects a time-course graph to use to derive an AIF for calculating parametric maps. Once a time-course graph is selected, the parametric maps are calculated at block 712. At block 714, the parametric maps are displayed in the GUI. For example, a parametric map or maps may be displayed as a semi-transparent overlay on the anatomical MR image. If, at block 716, the parametric maps generated from the selected AIF are considered acceptable, then the final results may be reported at block 718. For example, a report may be generated containing the location of the selected AIF, parameters derived from curve-fitting, MRI images from the dataset, and parametric maps. Alternatively, if the user determines the selected AIF does not provide appropriate parametric maps and data, the method returns to block 710 and the user may select a different time-course graph from the array of time-course graphs for use in deriving an AIF. Parametric maps based on the newly selected time-course graph are then computed and displayed.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

I claim:

1. A method for determining an arterial input function from a magnetic resonance image dataset, the method comprising:
providing a user interface configured to display at least one magnetic resonance image from the magnetic resonance image dataset and a plurality of time-course graphs simultaneously, the plurality of time-course graphs associated with a selected region of the at least one magnetic resonance image and each time-course graph having associated time-course data;
automatically annotating, using a processor, at least one displayed time-course graph with at least one element that highlights one or more portions of the at least one displayed time-course graph indicating fitness of the time-course data associated with the at least one time-course graph for use in deriving an arterial input function, wherein the at least one element is a shaded area of the at least one displayed time-course graph that indicates the fitness of the time-course data;
receiving a selection of a time-course graph from the plurality of time-course graphs; and
deriving an arterial input function from the time-course data associated with the selected time-course graph.

2. A method according to claim 1, further comprising:
generating at least one parametric map based on at least the arterial input function; and
displaying the at least one parametric map.

3. A method according to claim 2, wherein generating at least one parametric map comprises generating a plurality of parametric maps, each parametric map corresponding to a different hemodynamic parameter.

4. A method according to claim 2, wherein generating at least one parametric map comprises generating a plurality of parametric maps, each parametric map associated with a different slice location and generated using the arterial input function.

5. A method according to claim 2, wherein displaying the at least one parametric map comprises displaying the at least one parametric map simultaneously with the plurality of time-course graphs.

6. A method according to claim 2, wherein displaying the at least one parametric map comprises displaying the at least one parametric map as a semi-transparent overlay on a magnetic resonance image of a corresponding slice location.

7. A method according to claim 1, wherein the at least one magnetic resonance image comprises a plurality of pixels, each pixel having associated time-course data and wherein each time-course graph is generated by combining time-course data from neighboring pixels.

8. A method according to claim 7, wherein combining time-course data from neighboring pixels to generate the time-course graph comprises calculating an average of time-course data from neighboring pixels.

9. A method according to claim 1, wherein the at least one element is a best-fit curve derived from curve-fitting at least a portion of the time-course data associated with the at least one graph.

10. A method according to claim 1, wherein the at least one element is a mathematical parameter derived from curve-fitting at least a portion of the time-course data associated with the at least one graph.

11. A method according to claim 1, wherein the user interface further comprises a navigation tool configured to allow a user to select a region of the magnetic resonance image.

12. A method according to claim 11, wherein the navigation tool includes a zoom feature.

13. A method according to claim 11, wherein the navigation tool includes a panning feature.

14. A method according to claim 11, wherein the navigation tool is configured to zoom and pan the image using only mouse controls.

15. A method according to claim 1, wherein the magnetic resonance image and the plurality of time-course graphs are displayed side-by-side.

16. A method according to claim 1, wherein the shaded area of the at least one displayed time-course graph that indicates the fitness of the time-course data corresponds to at least one of a peak intensity measurement, a transit time parameter for a contrast agent, a signal baseline, an arrival time, a percentage of signal recovery or recovery relative to the baseline, or a negative enhancement integral.

17. A method according to claim 1, wherein the at least one element is a plurality of lines fitted to segments of the at least one displayed time-course graph.

18. A method according to claim 1, wherein the at least one element is a line corresponding to a threshold of the at least one displayed time-course graph that indicates the fitness of the time-course data.

19. A non-transitory computer-readable medium having computer-executable instructions for determining an arterial input function from a magnetic resonance image dataset, the computer-readable medium comprising:
program code for providing a user interface configured to display at least one magnetic resonance image from the magnetic resonance image dataset and a plurality of time-course graphs simultaneously, the plurality of time-course graphs associated with a selected region of the at least one magnetic resonance image and each time-course graph having associated time-course data;
program code for automatically annotating at least one displayed time-course graph with at least one element that highlights one or more portions of the at least one displayed time-course graph indicating fitness of the time-course data associated with the at least one time-course graph for use in deriving an arterial input function, wherein the at least one element is a shaded area of at least one of the displayed time-course graphs that indicates the fitness of the time-course data;
program code for receiving a selection of a time-course graph from the plurality of time-course graphs; and
program code for deriving an arterial input function from the time-course data associated with the selected time-course graph.

20. A non-transitory computer-readable medium according to claim 19, further comprising:
program code for generating at least one parametric map based on at least the arterial input function; and
program code for displaying the at least one parametric map.

21. An apparatus for determining an arterial input function from a magnetic resonance image dataset, the apparatus comprising:
a user interface configured to display at least one magnetic resonance image from the magnetic resonance image dataset and a plurality of automatically annotated time-course graphs simultaneously, the annotation including highlighting one or more portions of the displayed time-course graphs indicating a fitness thereof, and to receive a selection of a time-course graph from the plurality of time-course graphs to be used in deriving an arterial input function, wherein the highlighting is at least one shaded area of at least one of the displayed time-course graphs that indicates the fitness of the time-course data;

wherein the plurality of annotated time-course graphs are associated with a selected region of the at least one magnetic resonance image.

22. An apparatus according to claim 21, wherein the user interface further comprises a navigation tool configured to allow a user to select a region of the magnetic resonance image.

23. An apparatus for determining an arterial input function from a magnetic resonance image dataset, the apparatus comprising:

a processing unit programmed to execute a user interface configured to display at least one magnetic resonance image from the dataset and a plurality of automatically annotated timecourse graphs simultaneously, the annotation including highlighting one or more portions of the displayed time-course graphs indicating a fitness thereof, and to receive a selection of a time-course graph from the plurality of time-course graphs to be used in deriving an arterial input function, wherein the highlighting is at least one shaded area of at least one of the displayed time-course graphs that indicates the fitness of the time-course data;

wherein the plurality of annotated time-course graphs are associated with a selected region of the at least one magnetic resonance image.

* * * * *